United States Patent [19]

Sciavolino

[11] 4,090,017

[45] May 16, 1978

[54] 4-DEOXY-4-SUBSTITUTED AMINO DERIVATIVES OF OLEANDOMYCIN

[75] Inventor: Frank C. Sciavolino, East Lyme, Conn.

[73] Assignee: Pfizer Inc., New York, N.Y.

[21] Appl. No.: 765,478

[22] Filed: Feb. 4, 1977

[51] Int. Cl.² .............................................. C07H 17/08
[52] U.S. Cl. ...................................... 536/9; 424/180; 536/17
[58] Field of Search ....................................... 536/17, 9

[56] References Cited

U.S. PATENT DOCUMENTS

| | | | |
|---|---|---|---|
| 3,022,219 | 2/1962 | Celmer | 536/17 |
| 3,179,652 | 4/1965 | Celmer | 536/17 |
| 4,036,853 | 7/1977 | Sciavolino | 260/295 AM |

Primary Examiner—Johnnie R. Brown
Attorney, Agent, or Firm—Francis X. Murphy; Charles J. Knuth; Albert E. Frost

[57] ABSTRACT

Derivatives of oleandomycin, its 11-monoalkanoyl and 11,2'-dialkanoyl esters having at the 4"-position an amino group substituted with phenyl, benzyl or heterocyclylmethyl groups which may be substituted or unsubstituted, their preparation, and use as antibacterial agents is described.

20 Claims, No Drawings

4-DEOXY-4-SUBSTITUTED AMINO DERIVATIVES OF OLEANDOMYCIN

BACKGROUND OF THE INVENTION

1. Field of the Invention

This invention relates to a structurally unique group of macrolides and, more particularly, to derivatives of oleandomycin, its 11-mono- and 11,2'-dialkanoyl esters having at the 4"-position an amino group substituted with phenyl, benzyl or heterocyclylmethyl groups which may be substituted or unsubstituted, and to a method for their preparation. The compounds are antibacterial agents.

2. Description of the Prior Art

Oleandomycin, a macrolide antibiotic produced by fermentation, was first described in U.S. Pat. No. 2,757,123. It has the formula, the absolute configuration of which is shown below:

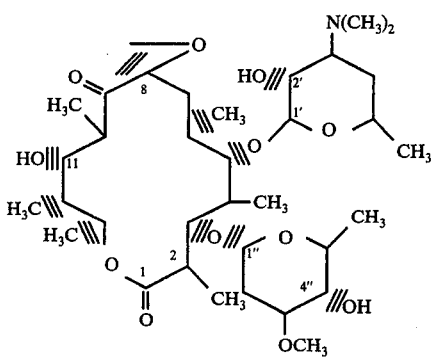

It consists of three main structural features: the L-oleandrose moiety, the desosamine moiety and the oleandolide moiety.

Derivatization of oleandomycin has focused primarily upon the formation of esters at one or more of three hydroxy groups located at the 2',4" and 11-positions. Mono-, di- and triacyl esters wherein the acyl moiety is derived from a lower aliphatic hydrocarbon monocarboxylic acid having from two to six carbon atoms are described in U.S. Pat. No. 3,022,219.

Aminohydrin derivatives of oleandomycin are reported by Kastrons et atl., Khim. Geterosikl Soedin (2), 168–71 (1974); C.A.80, 145986n (1974). The compounds, for which no utility is reported, are prepared by treating oleandomycin with a dialkylamine or a heterocyclic amine in a sealed tube for 20 hours at 30° C. The epoxide moiety at the 8-position is the site of reaction.

SUMMARY OF THE INVENTION

There has now been found a series of oleandomycin derivatives each of which exhibits valuable antibacterial activity in vitro and many of which exhibit in vivo activity by the parenteral and oral routes of administration, particularly against Gram-positive microorganisms. The compounds of this invention have formula II below wherein the wavy line connecting the substituted amino group at the 4"-position is generic to and embracive of both epimeric forms:

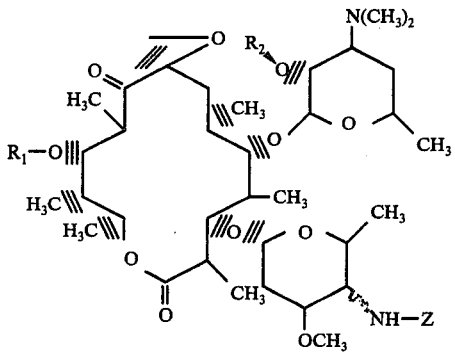

wherein each of $R_1$ and $R_2$ is selected from the group consisting of hydrogen, and alkanoyl having from two to three carbon atoms (acetyl and propionyl); Z is selected from the group consisting of a first subgroup consisting of

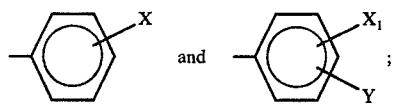

a second subgroup consisting of

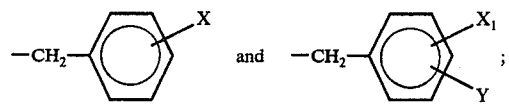

and a third subgroup consisting of

wherein

X is selected from the group consisting of hydrogen, chloro, bromo, fluoro, alkyl having from one to four carbon atoms, alkoxy having from one to four carbon atoms, hydroxy, mercapto, trifluoromethyl, $N(CH_3)_2$, cyano, thioalkyl having from one to four carbon atoms, sulfonylalkyl having from one to four carbon atoms, sulfamyl, sulfo, carbamyl, hydroxymethyl and carbalkoxy having from one to four carbon atoms in the alkoxy group;

$X_1$ is selected from the group consisting of chloro, bromo, fluoro, methyl, methoxy, hydroxy, mercapto and trifluoromethyl;

Y is selected from the group consisting of chloro, bromo, fluoro, methyl, methoxy and hydroxy;

and $X_1$ and Y when taken together are located on adjacent carbon atoms and are alkylenedioxy and are selected from the group consisting of methylenedioxy and ethylenedioxy;

and heterocyclyl is selected from the group consisting of (a) (2- and 3-)thienyl, (2- and 3-)furyl, (2-, 3- and 4-)pyridyl and (2- and 3-)pyrrolyl and substituted derivatives thereof wherein the substituent is selected from the group consisting of methyl, chloro, bromo, hydroxy and hydroxymethyl, and (b) 2-tetrahydrofuryl, 2-dihydropyranyl, 2-tetrahydropyranyl and morpholino.

Also included in the present invention are the pharmaceutically acceptable salts of compounds of formula II above. Representative of such salts, but not limited thereto, are the hydrochloride, hydrobromide, phosphate, sulfate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate, and aspartate.

Favored because of their greater biological activity relative to that of other compounds described herein are compounds of formula II wherein $R_1$ is acetyl, $R_2$ is hydrogen, and Z has the values shown below:

| Z | X | $X_1$ | Y |
|---|---|---|---|
| first subgroup | H and 2-X | $OCH_3$ | $OCH_3$ |
| second subgroup | H and 2-X | OH, Cl | $OCH_3$, Cl |
| third subgroup | O or N containing heterocyclyl | | |

Preferred compounds are those wherein $R_1$ is acetyl; $R_2$ is hydrogen and Z has the values shown below.

| Z | X | $X_1$ | Y |
|---|---|---|---|
| first subgroup | H, 2-$OCH_3$, 2-F | 2-$OCH_3$ or 3-$OCH_3$ | 4-$OCH_3$ |
| second subgroup | H | 4-OH or 3-Cl | 4-Cl |
| third subgroup | pyridyl, furyl, 2-dihydropyranyl, 2-tetrahydropyranyl | | |

Compounds of formula II, including the epimeric forms thereof, and their pharmaceutically acceptable salts are effective antibacterial agents against Gram-positive microorganisms, e.g., *Staphylococcus aureus* and *Streptococcus pyogenes,* in vitro and many are active in vivo via the parenteral and oral routes of administration. Many of the compounds (and their salts) are also active against certain Gram-negative microorganisms, such as cocci, e.g. *Pasteurella multocida* and *Neisseria sicca*.

DETAILED DESCRIPTION OF THE INVENTION

The structurally unique oleandomycin derivatives of this invention of formula II are prepared by reaction of the appropriate ketone of formula III:

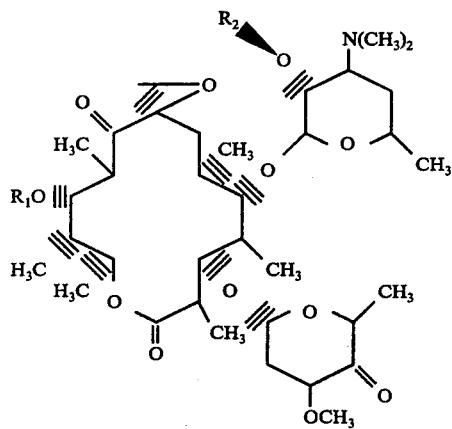

III wherein each of $R_1$ and $R_2$ is as previously defined, with the appropriate amine ($H_2$N-Z) reactant in a reaction-inert solvent to form an intermediate Schiff base compound which is then reduced to the corresponding substituted amino derivative. Alternatively, rather than conduct the process in this stepwise fashion, the overall process, a reductive amination, can be carried out by reacting a formula III compound and an appropriate amine ($H_2$N-Z) in the presence of a suitable reducing agent. The reaction when conducted in this manner is considered a one-step process since all reactants are added simultaneously, or both the ketone reactant and reducing agent are added simultaneously to the amine reactant, or the amine reactant and reducing agent are added simultaneously to the ketone. Regardless of the manner in which the reaction is carried out, the overall reaction is a reductive amination of the ketone (formula III) as previously noted. Since the amine reactant and reducing agent are more readily available than are the ketone compound of formula III, it is preferred to carry out the reaction in a stepwise manner to first form the intermediate Schiff base which is then reduced. The Schiff base intermediate need not be isolated but can be if desired. An inert atmosphere can be used but is not required. Regardless of the manner in which it is carried out, the process is generally conducted in a reaction-inert solvent; i.e., one which does not react with reactants or products.

The molar ratio of ketone compound to amine reactant can vary widely, e.g., from about 1:1 to about 1:10. Molar ratios of less than 1:1 are avoided for economic reasons to insure maximum reaction of the ketone compound, normally the least available of the reactants. Ratios of greater than 1:10 are seldom used since they do not appear to improve the yield of final product.

Suitable reaction-inert solvents are alcohols having from one to four carbon atoms, ethylene glycol, propylene glycol, tetrahydrofuran, dioxane, diethyl ether, benzene, toluene, acetonitrile, methylene chloride. The favored solvents are polar solvents such as alcohols and acetonitrile which afford a faster rate of reaction relative to that of non-polar solvents. When using a 2'-alkanoyl or an 11,2'-dialkanoyl derivative of formula III or IV as reactant, a secondary alcohol, and preferably isopropanol, is used as solvent to avoid removal of the 2'-alkanoyl group; unless, of course, removal of such group is desired.

The reaction can be carried out at temperatures from about $-10°$ to about $50°$ C. The temperature range of from about $10°$ to about $30°$ C. is favored since it permits a satisfactory rate of reaction and satisfactory yields of product.

The reaction between the ketone and amine reactant is acid-catalyzed. For convenience, the amine reactant is generally used in the form of an acid addition salt with a strong mineral acid, e.g., hydrochloric, hydrobromic, hydriodic, sulfuric, nitric or phosphoric acid. Alternatively, the amine reactant can be used as the free base form and the appropriate acid added to form the acid addition salt in situ. The hydrochloride salts are the favored acid addition salts primarily because of their availability. The presence of the acid addition salt form of the amine reactant tends to accelerate Schiff base formation and to increase the yield of desired product. The molar ratio of acid to amine reactant used is desirably in the range of from about 0.5:1.0 to 1:1.5. At ratios outside these ranges, the yield of the final product is reduced. Best results are generally achieved with equimolar or approximately equiomolar proportions (e.g., 0.8:1 to 1:1.2) of acid to amine reactant.

An alternative method for preparing compounds of this invention wherein Z is selected from the second or third subgroups comprises condensation of the appropriate aldehyde $Z_1$-CHO with the appropriate amine reactant of formula IV:

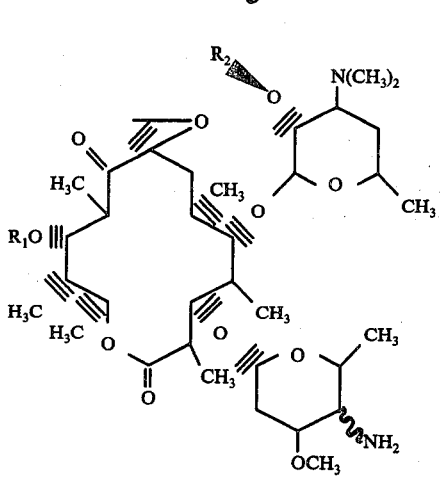

in a reaction-inert solvent at a temperature of from about −10° to about 50° C. The reaction mixture thus produced, which is believed to contain a Schiff base, is then treated with a reducing agent to produce the desired product having formula II. This process is conducted under essentially the same conditions as are recited above for the first method. The only parameter in which a difference exists, and this only a minor difference, is the temperature range. The second method appears to permit a somewhat lower range as the preferred range; namely, from about −10° to 10° C.

The reaction of this method is also acid catalyzed. The amine reactant of formula IV can be in the form of an acid addition salt with any of a variety of acids, such as a strong mineral acid. e.g., hydrochloric, hydrobromic, hydriodic, sulfuric, nitric or phosphoric acid; an alkanoic acid having from one to four carbon atoms, e.g., formic, acetic, propionic or butyric acids. Alternatively, said amine reactant can be used as the free base form and an appropriate acid added to form the acid addition salt in situ. The acetate and hydrochloride salts are the favored acid addition salts primarily because of their availability. The presence of the acid addition salt form of the amine reactant tends to accelerate Schiff base formation and to increase the yield of desired product. The molar ratio of acid to amine reactant used is desirably in the range of from about 0.5:1.0 to 1:1.5. At ratios outside these ranges, the yield of the final product is reduced. Best results are generally achieved with equimolar or approximately equimolar proportions (e.g., 0.8:1 to 1:1.2) of acid to amine reactant.

While in principle a variety of reducing agents can be used in either method to achieve the overall reaction of reductive amination, in practice care must be exercised in the choice of reducing agents because of the presence of other reducible groups in the ketone reactant (formula III) or amine reactant (formula IV).

The favored reducing agent is sodium cyanoborohydride since it effectively accomplishes only the desired reduction and requires relatively mild conditions. Further, it is not affected by by-product water present in the reaction mixture. It is used in molar ratios of from about one to about three moles per mole of ketone reactant of formula III or of formula Z—CHO.

Other reducing agents which can be used are hydrogen in the presence of palladium-on-charcoal and borane-dimethylamine complex.

The above-described processes generate water which need not be removed from the reaction mixtures. However, if desired, the by-product water can be removed by conducting the reaction at reduced pressure or by "effectively" removing it by the use of molecular sieves as adsorbent for the water. Suitable adsorbents are the natural and synthetic crystalline aluminosilicates. The latter adsorbents are favored because of their greater water-loading capacity relative to the natural crystalline aluminosilicates. Included among such adsorbents are chabazite, a naturally occurring material, the synthetic "Linde Molecular Sieves" produced and distributed by the Linde Company, such as Types 4A, 5A and 13X, and the "Microtraps" produced by the Davison Chemical Company. Such materials sorb and thus effectively remove water from the reaction medium. The exhausted or partially exhausted aluminosilicate is separated from the reaction mixture by filtration or decantation.

When using a molecular sieve to effectively remove by-product water, it is necessary to use a reaction-insert solvent such as benzene, toluene, dimethyl sulfoxide, ethanol or propanol. Atmospheric pressure is favored for reasons of simplicity of equipment and ease of operation although sub- or superatmospheric pressures can be used if desired. The quantity of molecular sieve to be used depends upon the reaction conditions such as temperature, solvent, and on the nature of the molecular sieve itself and is best determined by experiment. In general, however, a quantity sufficient to sorb the theoretical amount of by-product water should be used. In actual practice an excess of molecular sieve is advantageous since it assures more complete reaction.

The reaction mixture, free of molecular sieve, is then reduced as described above.

When the formula III reactant is an 11-monoalkanoyl or 11-hydroxy derivative, the reaction produces a mixture of epimers (represented by a wavy line in formula II compounds) which can be separated, if desired. Column chromatography of a chloroform solution of the crude product on silica gel and elution with appropriate solvents, e.g., chloroform-3% methanol, offers a convenient method for separating the epimers. In the present description and illustrations, it is understood that although the compounds are listed as 4"-substituted amino derivatives, both epimers and mixtures thereof are included.

It has been observed that when an 11,2'-dialkanoyl-4"-deoxy-4"-oxooleandomycin is reacted with the herein-described aniline reactants, as described above, the product consists predominantly of a single epimer.

Diester compounds of formula II; i.e., each of $R_1$ and $R_2$ is alkanoyl, can also be prepared by acylation of the corresponding 11-monoalkanoyl ($R_1$ = alkanoyl; $R_2$ = H) compound by standard procedures known to those skilled in the art, and as exemplified herein. In this manner, preparation of diester compounds wherein the ester groups differ is readily achieved.

Acid addition salts of the compounds of this invention are readily prepared by treating formula II compounds with an equimolar amount of the appropriate acid in a reaction-inert solvent for the formula II compound. The acid addition salts are recovered by filtration if they are insoluble in the reaction-inert solvent, by precipitation, by addition of a non-solvent for said salt, or by evaporation of the solvent.

The 11-mono-alkanoyl- and 11,2'-dialkanoyl-4"-deoxy-4"-oxo-oleandomycin reactants (formula III) are prepared by oxidation of the appropriate 11,2'-dialkanoyl-oleandomycin with, for example, N-chlorosuccinimide, to the corresponding 11,2'-dialkanoyl-4"-deoxy-4"-oxo-oleandomycin. Solvolysis of the diester by treatment with methanol affords the 11-monoester product. In like manner, 4"-deoxy-4"-oleandomycin is prepared from 2'-alkanoyl-oleandomycin by oxidation and hydrolysis.

The 11-mono-alkanoyl- and 11,2'-dialkanoyl-4"-deoxy-4"-amino-oleandomycin reactants (formula IV) are prepared by reductive amination of the corresponding 11-mono-alkanoyl-, 2'-monoalkanoyl- and 11,2'-dialkanoyl-4"-deoxy-4"-oxo-oleandomycins using palladium-on-charcoal, hydrogen and ammonium acetate in a suitable solvent, ($CH_3OH$, $i-C_3H_7OH$). Alternatively, sodium cyanoborohydride can be used as reducing agent in place of palladium-on-charcoal and hydrogen. The de-esterified derivative is conveniently prepared by hydrolysis of the corresponding 2'-monoalkanoyl-4''-deoxy-4''-amino-oleandomycins.

The novel oleandomycin derivatives described herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated four, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

EXAMPLE 1

11-Acetyl-4''-deoxy-4''-anilino-oleandomycin

To a solution of aniline (15.0 g., 0.16 mole) in methanolic-hydrogen chloride (65 ml., 0.16 mole, of 2.5 molar) under an atmosphere of nitrogen and cooled in an ice bath is added with stirring a solution of 11-acetyl-4''-deoxy-4''-oxo-oleandomycin (20.0 g., 0.027 mole) in methanol (100 ml.). The resulting amber-colored solution is stirred for fifteen minutes and is then treated dropwise with sodium cyanoborohydride (1.45 g., 0.0198 mole) in methanol (70 ml.) over a period of 1.5 hours. The reaction mixture is stirred for an additional three hours and is then poured into a mixture of ethyl acetate (1.2 l.) and water (1.2 l.). The pH is adjusted to 9.5 (aqueous 6N NaOH) and the aqueous layer discarded. Fresh water (1.2 l.) is added to the ethyl acetate solution and the pH adjusted to 4.0 with hydrochloric acid (6N). The ethyl acetate phase is separated, water (1.2 l.) added and the pH brought to 9.5 by means of aqueous sodium hydroxide. The ethyl acetate phase is separated, washed with water (2 × 500 ml.), saturated with sodium chloride solution (1 × 500 ml.) and then dried ($Na_2SO_4$). Evaporation under reduced pressure affords an amber oil (25 g.).

The oil is dissolved in chloroform (50 ml.) and chromatographed on a silica gel (400 g.) column (60 cm. × 4 cm.) using chloroform-4% methanol as eluant. Ten ml. fractions are collected. Fractions 261-310 are combined and concentrated under reduced pressure to give 5.85 g. of impure product as a white foam. The foam is taken up in acetone (50 ml.) and chromatographed on a silica gel (400 g.) column (60 cm. × 4 cm.) using acetone as eluant. Fractions (10 ml. each) 61-240 are combined and evaporated to dryness under reduced pressure. Yield 4.0 g., m.p. 99°–109° C. of a mixture of epimeric anilino substituted products.

Mass Spec. m/e = 158, 220, 351.

NMR (60 MHz) $\delta_{CDCl_3}^{TMS}$ (ppm): 7.00 (bm, 5H), 3.46 (s,1H), 3.43 (s, 2H), 2.70 (m, 2H), 2.33 (s, 6H), 2.10 (s, 3H).

The following compounds are similarly prepared but using the appropriate substituted aniline in place of aniline. In the table below, the column headed $C_1$ indicates the solvent system used to purify the products via silica gel chromatography. Only one such treatment was used. In each instance a mixture of epimeric substituted anilino products is obtained.

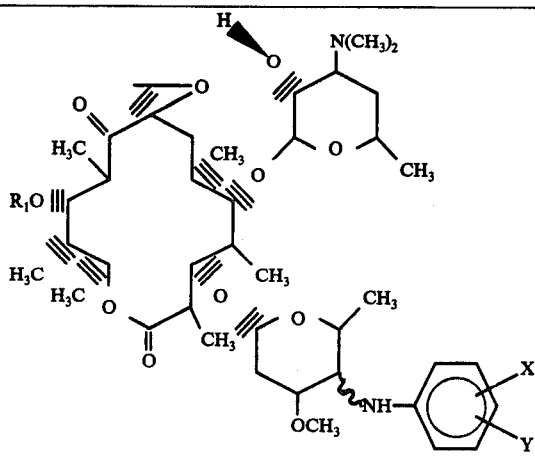

| Ex. | Ketone g. | Substituted Aniline g. | X | Y | $C_1$ | yield (g.) | MS (m/e) | NMR (60 MHz) $\delta_{CDCl_3}^{TMS}$(ppm) | M.P.[a] (° C.) | $R_1$[b] |
|---|---|---|---|---|---|---|---|---|---|---|
| 2 | 3.0 | 4.5 | 2-F | H | acetone | 0.66 | | 6.93(bm,4H),3.46(s,1H),3.40(s,2H),2.71(m,2H),2.46(s,2H),2.43(s,4H),2.10(s,3H). | | Ac |
| 3 | 3.0 | 4.5 | 3-F | H | acetone | | | 6.40(bm,4H),3.43(s,1H),3.40(s,2H),2.66(m,2H),2.33(s,6H),2.10(s,3H). | | Ac |
| 4 | 3.0 | 4.5 | 4-F | H | acetone | | | 6.73(q,4H),3.43(s,1H),3.40(s,2H),2.65(m,2H),2.31(s,6H),2.08(s,3H). | | Ac |
| 5 | 5.0 | 8.3 | 2-OCH$_3$ | H | acetone | 0.54 | 158,250 | 6.80(m,4H),3.90(s,2H),3.86(s,1H),3.43(s,1H),3.40(s,2H),2.66(m,2H),2.36(s,6H),2.10(s,3H) | 98–100 | Ac |
| 6 | 5.0 | 4.1 | 3-OCH$_3$ | H | CHCl$_3$— 4% CH$_3$OH | 0.85 | 158,250, 335,351, 411. | 6.28(m,4H),3.78(s,3H),3.43(s,1H),3.38(s,2H),2.70(m,2H),2.30(s,6H),2.08(s,3H). | 93–104 | Ac |
| 7 | 5.0 | 4.1 | 4-OCH$_3$ | H | CHCl$_3$— 3% CH$_3$OH | 1.1 | 158,250, 351,411. | 6.76(q,4H),3.76(s,3H),3.43(s,1H),3.40(s,2H),2.70(m,2H),2.30(s,6H),2.10(s,3H). | 94–100 | Ac |
| 8 | 5.0 | 8.6 | 2-Cl | H | acetone | 0.92 | 158,174, 254,256, 351. | 6.88(m,4H),3.45(s,1H),3.41(s,2H),2.66(m,2H),2.36(s,6H),2.10(s,3H). | 90–95 | Ac |
| 9 | 5.0 | 4.3 | 3-Cl | H | CHCl$_3$— 3% CH$_3$OH | 1.5 | 158,254, 256,351. | 6.90(bm,4H),3.46(s,1H),3.40(s,2H),2.70(m,2H),2.33(s,2H),2.10(s,3H). | 109–120 | Ac |
| 10 | 5.0 | 4.3 | 4-Cl | H | CHCl$_3$— 4% CH$_3$OH | 1.8 | 158,254, 256,351. | 6.93(q,4H),3.43(s,1H),3.40(s,2H),2.66(m,2H),2.30(s,6H),2.10(s,3H). | 107–118 | Ac |
| 11 | 5.0 | 5.8 | 2-Br | H | CHCl$_3$— 4% CH$_3$OH | 2.0 | 158,298, 300,351. | 7.03(m,4H),3.43(s,1H),3.40(s,2H),2.66(m,2H),2.30(s,6H),2.06(s,3H). | 97–109 | Ac |
| 12 | 5.0 | 5.8 | 4-Br | H | CHCl$_3$— 4% CH$_3$OH | 2.0 | 158,298, 300,351. | 6.63(q,4H),3.41(s,1H),3.38(s,2H),2.66(m,2H),2.30(s,6H),2.06(s,3H). | | Ac |
| 13 | 5.0 | 5.4 | 2-CF$_3$ | H | acetone | 0.59 | 158,288, 351. | 6.91(m,4H),3.83(s,3H),2.65(m,2H),2.33(s,6H),2.08(s,3H). | 99–108 | Ac |
| 14 | 5.0 | 3.6 | 2-CH$_3$ | H | acetone | 1.3 | 158,234, 351. | 7.00(m,4H),3.46(s,1H),3.36(s,2H),2.70(m,2H),2.33(s,6H),2.20(s,2H),2.16(s,1H),2.10(s,3H). | 100–112 | Ac |
| 15 | 5.0 | 3.6 | 3-CH$_3$ | H | CHCl$_3$— 4% CH$_3$OH | 1.0 | 158,234, 335,351, 411. | 2.70(s,2H),2.31(s,6H),2.30(s,3H),2.10(s,3H). | | |
| 16 | 5.0 | 3.6 | 4-CH$_3$ | H | acetone | 2.1 | 158,234, 351. | 2.33(s,6H),2.26(s,3H),2.10(s,3H). | 99–108 | Ac |
| 17 | 5.0 | 4.0 | 2-CN | H | acetone | 0.35 | 158,174, 245,351, 411. | 2.66(m,2H),2.35(s,3H),2.11(s,3H). | 98–110 | Ac |
| 18 | 5.0 | 4.1 | 2-CH$_2$OH | H | CHCl$_3$— 4% CH$_3$OH | 0.88 | 158,250, 335,351, 411. | 6.96(m,4H),4.73(bs,2H),3.33(s,3H),2.68(m,2H),2.31(s,6H),2.10(s,3H). | | Ac |
| 19 | 10.0 | 10.2 | 2-COOCH$_3$ | H | CHCl$_3$— 3% CH$_3$OH | 1.7 | 158,278, 335,351, 411. | 7.03(bm,4H),3.88(s,3H),3.45(s,1H),3.36(s,2H),2.70(m,2H),2.31(s,6H),2.08(s,3H). | | Ac |
| 20[c] | 2.3 | 3.0 | 2-N(CH$_3$)$_2$ | H | CHCl$_3$— 3% CH$_3$OH | 0.74 | 158,263, 335,351, 411. | 6.71(s,4H),3.38(s,3H),3.81(s,6H),2.66(m,2H),2.33(s,6H),2.08(s,3H). | | Ac |
| 21 | 5.0 | 4.6 | 2-CONH$_2$ | H | CHCl$_3$— 3% CH$_3$OH | | 158,263, 350. | 4.05(m,4H),3.45(s,1.5H),3.36(s,1.5H),2.68(m,2H),2.31(s,6H),2.06(s,3H). | 125–135 | Ac |
| 22 | 3.0 | 4.4 | 4-OH | H | CHCl$_3$— 2% CH$_3$OH | 0.72 | | 6.71(m,4H),3.45(s,1H),3.40(s,2H),2.70(m,2H),2.33(s,6H),2.10(s,3H). | 114(dec.) | Ac |
| 23 | 5.0 | 4.1 | 2-CH$_3$ | 6-CH$_3$ | CHCl$_3$— 3% CH$_3$OH | 0.60 | 158,248, 335,351. | 6.51(m,3H),3.18(s,3H),2.68(m,2H),2.33(s,9H),2.20(s,3H),2.08(s,3H). | | Ac |
| 24 | 5.0 | 4.7 | 2-CH$_3$ | 4-Cl | CHCl$_3$— 4% CH$_3$OH | 1.7 | 158,268, 270,335, 351,411. | 6.90(m,3H),3.43(s,1H),3.38(s,2H),2.70(m,2H),2.33(s,6H),2.21(s,3H),2.10(s,3H). | | Ac |
| 25 | 5.0 | 5.5 | 3-Cl | 4-Cl | CHCl$_3$— 4% CH$_3$OH | 2.2 | 158,288, 290,292, 335,351, 411. | 7.20(s,1H),6.76(m,2H),3.46(2,1H),3.40(s,2H),2.70(m,2H),2.30(s,6H),2.10(s,3H). | 98–114 | Ac |
| 26 | 5.0 | 5.2 | 2-OCH$_3$ | 4-OCH$_3$ | CHCl$_3$— 4% CH$_3$OH | 1.4 | 158,280, 335. | 6.46(m,3H);3.83(s,2H),3.76(s,4H),3.40(s,1H),3.36(s,2H),2.66(m,2H),2.30(s,6H),2.06(s,3H). | 99–107 | Ac |
| 27 | 2.5 | 2.5 | 3-OCH$_3$ | 4-OCH$_3$ | CHCl$_3$— 4% CH$_3$OH | 0.28 | 158,280, 335,351, 411. | 6.58(m,3H),3.88(s,3H),3.81(s,3H),3.41(s,3H),2.70(m,2H),2.31(s,6H),2.08(s,3H). | 98–108 | Ac |
| 28 | 5.0 | 5.2 | 3-OCH$_3$ | 5-OCH$_3$ | CHCl$_3$— 4% CH$_3$OH | 1.1 | 158,280, 335,351 | 5.96(m,3H),3.81(s,6H),3.46(s,1H),3.43(s,2H),2.71(s,2H),2.35(s,6H),2.11(s,3H). | | Ac |

-continued

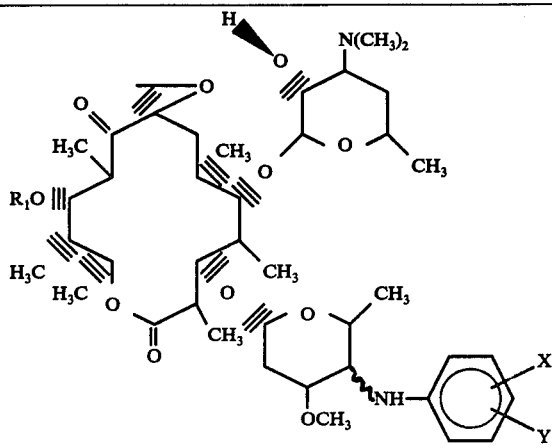

| Ex. | Ketone g. | Substituted Aniline g. | X | Y | C₁ | yield (g.) | MS (m/e) | NMR (60 MHz) $\delta_{CDCl_3}^{TMS}$(ppm) | M.P.[a] (° C.) | R₁[b] |
|---|---|---|---|---|---|---|---|---|---|---|
| 29 | 3.5 | 9.7 | 3-CF₃ | 2-Cl | CHCl₃— 4% CH₃OH | 1.5 | 411. | 6.7-7.6(m,aromatic H),3.43(s,3H),2.66(d,2H), 2.33(s,6H),2.10(s,3H). | | Ac |
| 30 | 5.0 | 2.0 | 2-OCH₃ | H | CHCl₃—2% i-C₃H₇OH | 0.18 | 158,250 | 6.75(bs,4H),3.86(s,2H),3.78(s,1H),3.40(s, 1H),3.36(s,2H),2.83(m,2H),2.16(s,6H). | | H |
| 31 | 4.0 | 5.4 | 2-COOCH₃ | H | CHCl₃—3% i-C₃H₇OH | 0.19 | 158,278, 386 | 7.4(bm,4H),3.88(s,2H),3.85(s,1H),3.43(s, 2H),3.36(s,1H),2.76(m,2H),2.23(s,6H). | | H |

[a]The melting points observed are broad since the products are a mixture of epimers.
[b]Ac = Acetyl
[c]The product of Example 20 is extracted with ethyl acetate at pH 6.0.

EXAMPLE 32

Epimeric 11-Acetyl-4''-deoxy-4''-(2-hydroxyanilino)-oleandomycins

The procedure of Example 1 is repeated but using 5 g. of 11-acetyl-4''-deoxy-4''-oxo-oleandomycin, 3.6 g. of o-aminophenol and 310 mg. of 85% sodium cyanoborohydride. The reaction mixture is worked up according to the procedure of Example 1, the oily reaction product taken up in chloroform and chromatographed on silica gel using chloroform-3% methanol as eluant. Ten ml. fractions are collected. Fractions 81–97 contain a mixture of epimers. Fractions 98–150 are found on thin layer chromatography to contain a single compound. Evaporation of the eluate affords the compounds as a tan solid; m.p. 118°–120° C., 720 mg.

Fractions 151–200 contains a mixture of epimers and fractions 201–250 are found to contain a single compound, the epimer of the above-mentioned product.

The configuration of these two epimeric compounds has not yet been established.

The NMR spectra of these epimers are presented below.

NMR (60 MHz) $\delta_{CDCl_3}^{TMS}$ (ppm):
(a) First Epimer
6.86 (bs, 4H), 3.53 (s, 3H), 2.70 (m,2H), 2.31 (s, 6H), 2.11 (s, 3H).
(b) Second Epimer
6.83 (bm, 4H), 3.51 (s,3H), 2.73 (m,2H), 2.38 (s, 6H), 2.10 (s, 3H).

The mass spectra of the epimers is identical; m/e = 158, 236, 335, 351, 411.

EXAMPLE 33

The procedure of Example 1 is repeated but using the appropriate 4''-deoxy-4''-oxo-oleandomycin reactant and the appropriate aniline as reactants to produce the following compounds:

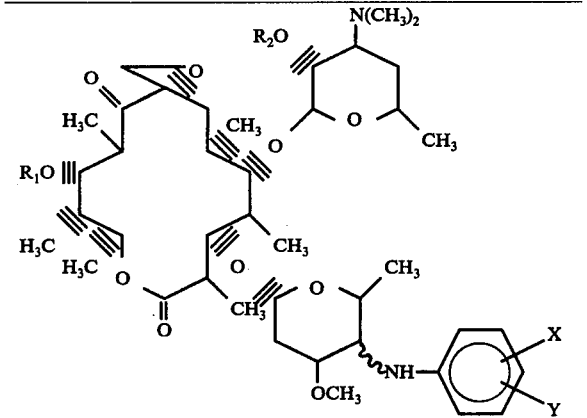

| R₁ | X | Y | R₂ |
|---|---|---|---|
| COCH₃ | 2-C₂H₅ | H | H |
| COCH₃ | 4-C₂H₅ | H | H |
| COCH₃ | 3-n-C₃H₇ | H | COCH₃ |
| COCH₃ | 2-i-C₃H₇ | H | H |
| COCH₃ | 2-n-C₄H₉ | H | COCH₃ |
| COCH₃ | 4-n-C₄H₉ | H | H |
| COCH₃ | 4-t-C₄H₉ | H | H |
| COCH₃ | 3-CF₃ | H | H |
| COCH₃ | 4-CF₃ | H | COCH₃ |
| COCH₃ | 3-CONH₂ | H | H |
| COCH₃ | 2-SH | H | H |
| COCH₃ | 4-SH | H | COCH₂CH₃ |
| COCH₃ | 3-OH | H | H |
| COCH₃ | 2-SO₂NH₂ | H | H |
| COCH₃ | 3-SO₂NH₂ | H | COCH₃ |
| COCH₃ | 4-SO₂H | H | COCH₃ |
| COCH₃ | 2-SO₃H | H | H |
| COCH₃ | 3-CH₂OH | H | H |
| COCH₃ | 3-SO₂CH₃ | H | H |
| COCH₃ | 2-OC₂H₅ | H | COCH₂CH₃ |
| COCH₃ | 4-O-n-C₄H₉ | H | H |
| COCH₃ | 4-O-i-C₃H₇ | H | H |
| COCH₃ | 4-COOCH₃ | H | COCH₂CH₃ |
| COCH₃ | 3-COO-n-C₄H₉ | H | H |
| COCH₃ | 4-COOC₂H₅ | H | H |
| COCH₃ | 2-SCH₃ | H | H |
| COCH₃ | 3-SC₂H₅ | H | H |

-continued

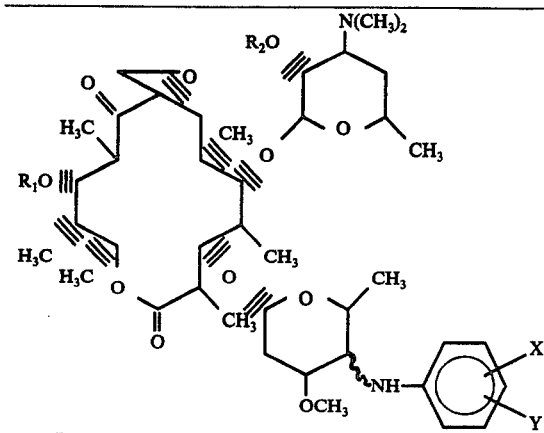

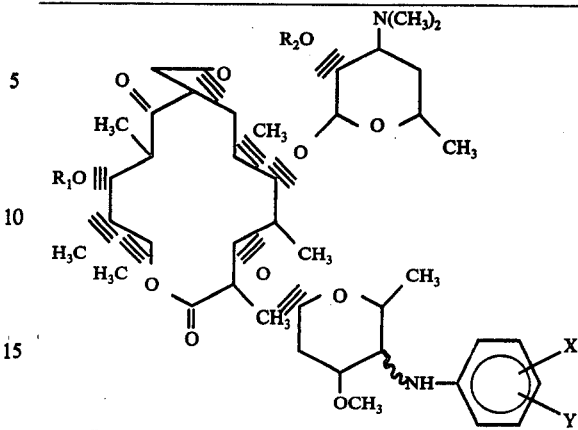

| R₁ | X | Y | R₂ |
|---|---|---|---|
| COCH₃ | 4-S-n-C₄H₉ | H | COCH₃ |
| COCH₃ | 2-SO₂CH₃ | H | H |
| COCH₃ | 2-SO₂CH₃ | H | H |
| COCH₃ | 4-SO₂CH₃ | H | H |
| COCH₃ | 3-SO₂C₂H₅ | H | COCH₃ |
| COCH₃ | 3-SO₂C₂H₅ | H | H |
| COCH₃ | 4-SO₂-n-C₄H₉ | H | COCH₃ |
| COCH₃ | 4-SO₂-n-C₄H₉ | H | H |
| COCH₃ | 2,3-O—CH₂—O— | | COCH₃ |
| COCH₃ | 3,4-O—CH₂—O— | | H |
| COCH₃ | 3,4-O—CH₂CH₂—O— | | H |
| COCH₃ | 2,3-O—CH₂CH₂—O— | | COCH₂CH₃ |
| COCH₂CH₃ | 2F | H | COCH₂CH₃ |
| COCH₂CH₃ | 2-OCH₃ | H | H |
| COCH₂CH₃ | 4-OCH₃ | H | COCH₂CH₃ |
| COCH₂CH₃ | 3-CH₂OH | H | H |
| COCH₂CH₃ | 3-CH₃ | H | H |
| COCH₂CH₃ | 4-C₂H₅ | H | H |
| COCH₂CH₃ | 4-t-C₄H₉ | H | COCH₂CH₃ |
| COCH₂CH₃ | 3-CF₃ | H | H |
| COCH₂CH₃ | 3-CN | H | H |
| COCH₂CH₃ | 4-CN | H | COCH₂CH₃ |
| COCH₂CH₃ | 4-N(CH₃)₂ | H | H |
| COCH₂CH₃ | 2-COOCH₃ | H | H |
| COCH₂CH₃ | 4-COO-n-C₄H₉ | H | COCH₂CH₃ |
| COCH₂CH₃ | 3-COOC₂H₅ | H | H |
| COCH₂CH₃ | 3-Cl | H | H |
| COCH₂CH₃ | 4-Br | H | COCH₂CH₃ |
| COCH₂CH₃ | 4-SO₃H | H | H |
| COCH₂CH₃ | 4-Cl | H | COCH₂CH₃ |
| COCH₂CH₃ | H | H | H |
| COCH₂CH₃ | 4-t-C₄H₉ | H | H |
| COCH₂CH₃ | 3-i-C₃H₇ | H | H |
| COCH₂CH₃ | 2-C₂H₅ | H | COCH₂CH₃ |
| COCH₂CH₃ | 3-OC₂H₅ | H | H |
| COCH₂CH₃ | 4-O-n-C₄H₉ | H | H |
| COCH₂CH₃ | 2-OH | H | COCH₃ |
| COCH₂CH₃ | 3-OH | H | H |
| COCH₂CH₃ | 4-OH | H | H |
| COCH₂CH₃ | 2-CONH₂ | H | H |
| COCH₂CH₃ | 4-CONH₂ | H | H |
| COCH₂CH₃ | 2-SH | H | COCH₂CH₃ |
| COCH₂CH₃ | 4-SH | H | H |
| COCH₂CH₃ | 2-SCH₃ | H | H |
| COCH₂CH₃ | 3-SCH₃ | H | H |
| COCH₂CH₃ | 4-S-n-C₄H₉ | H | H |
| COCH₂CH₃ | 3-SC₂H₅ | H | COCH₃ |
| COCH₂CH₃ | 2-SO₂CH₃ | H | H |
| COCH₂CH₃ | 3-SO₂C₂H₅ | H | H |
| COCH₂CH₃ | 4-SO₂-n-C₄H₉ | H | COCH₂CH₃ |
| COCH₂CH₃ | 2-SO₂CH₃ | H | H |
| COCH₂CH₃ | 3-SO₂C₂H₅ | H | H |
| COCH₂CH₃ | 4-SO₂-n-C₄H₉ | H | COCH₂CH₃ |
| COCH₂CH₃ | 3-SO₂NH₂ | H | COCH₂CH₃ |
| COCH₂CH₃ | 4-SO₂NH₂ | H | H |
| COCH₂CH₃ | 2-CH₂OH | H | H |
| COCH₂CH₃ | 3-CH₂OH | H | COCH₃ |
| COCH₂CH₃ | 2-COOCH₃ | H | H |
| COCH₂CH₃ | 4-COO-i-C₃H₇ | H | H |
| COCH₂CH₃ | 3-COO-n-C₄H₉ | H | H |
| COCH₂CH₃ | 2,3-O—CH₂—O— | | H |
| COCH₂CH₃ | 3,4-O—CH₂CH₂—O— | | COCH₂CH₃ |
| COCH₂CH₃ | 2,3-O—CH₂CH₂—O— | | H |
| COCH₃ | 2-Cl | 6-Cl | H |
| COCH₃ | 3-Cl | 4-Br | H |
| COCH₃ | 2-Br | 4-F | COCH₃ |
| COCH₃ | 2-Cl | 3-F | H |
| COCH₃ | 2-F | 4-F | H |
| COCH₃ | 2-F | 6-F | H |
| COCH₃ | 2-CH₃ | 4-F | COCH₃ |
| COCH₃ | 3-CH₃ | 5-Cl | H |
| COCH₃ | 4-CH₃ | 3-Br | H |
| COCH₃ | 2-Br | 4-OCH₃ | COCH₃ |
| COCH₃ | 3-Cl | 4-OCH₃ | H |
| COCH₃ | 4-F | 3-OCH₃ | H |
| COCH₃ | 2-OH | 6-Br | H |
| COCH₃ | 2-OH | 5-Cl | COCH₂CH₃ |
| COCH₃ | 5-OH | 2-Cl | H |
| COCH₃ | 4-OH | 3-Cl | H |
| COCH₃ | 4-OH | 2-F | COCH₂CH₃ |
| COCH₃ | 2-SH | 5-Cl | H |
| COCH₃ | 4-SH | 3-Cl | COCH₃ |
| COCH₃ | 4-SH | 3-Br | H |
| COCH₃ | 4-SH | 2-F | H |
| COCH₃ | 2-CF₃ | 4-F | COCH₃ |
| COCH₃ | 2-CF₃ | 4-Br | H |
| COCH₃ | 5-CF₃ | 2-Cl | H |
| COCH₃ | 5-CF₃ | 2-Cl | H |
| COCH₃ | 2-CH₃ | 4-CH₃ | H |
| COCH₃ | 2-CH₃ | 4-OCH₃ | COCH₃ |
| COCH₃ | 5-CH₃ | 2-OCH₃ | H |
| COCH₃ | 6-CH₃ | 2-OH | COCH₃ |
| COCH₃ | 2-CH₃ | 4-OH | H |
| COCH₃ | 5-OCH₃ | 2-OH | H |
| COCH₃ | 4-OCH₃ | 3-OH | COCH₂CH₃ |
| COCH₃ | 2-OH | 4-OH | H |
| COCH₃ | 3-SH | 4-OH | H |
| COCH₂CH₃ | 2-OCH₃ | 4-OCH₃ | H |
| COCH₂CH₃ | 3-OCH₃ | 5-OCH₃ | COCH₂CH₃ |
| COCH₂CH₃ | 3-Cl | 4-Cl | H |
| COCH₂CH₃ | 2-CH₃ | 6-CH₃ | COCH₂CH₃ |
| COCH₂CH₃ | 2-F | 4-F | COCH₃ |
| COCH₂CH₃ | 2-Br | 5-F | H |
| COCH₂CH₃ | 3-Br | 4-Br | H |
| COCH₂CH₃ | 3-F | 2-Cl | COCH₂CH₃ |
| COCH₂CH₃ | 4-OCH₃ | 2-Cl | COCH₂CH₃ |
| COCH₂CH₃ | 4-OCH₃ | 3-Br | H |
| COCH₂CH₃ | 3-OCH₃ | 4-F | H |
| COCH₂CH₃ | 2-CH₃ | 4-F | H |
| COCH₂CH₃ | 2-CH₃ | 4-Cl | H |
| COCH₂CH₃ | 2-CH₃ | 5-Br | COCH₂CH₃ |
| COCH₂CH₃ | 4-SH | 2-CH₃ | H |
| COCH₃ | 5-SH | 2-CH₃ | H |
| COCH₃ | 2-SH | 5-OCH₃ | COCH₂CH₃ |
| COCH₃ | 5-CF₃ | 2-CH₃ | H |
| COCH₃ | 6-CF₃ | 3-OCH₃ | COCH₂CH₃ |
| COCH₃ | 2-CF₃ | 5-OH | H |
| COCH₂CH₃ | 2-OH | 6-OH | COCH₃ |
| COCH₂CH₃ | 2-CH₃ | 4-OCH₃ | H |
| COCH₂CH₃ | 3-CH₃ | 6-Cl | H |
| COCH₂CH₃ | 2-CH₃ | 5-OH | H |
| COCH₂CH₃ | 5-CH₃ | 2-OH | H |
| COCH₂CH₃ | 2-CH₃ | 6-OH | COCH₃ |
| COCH₂CH₃ | 5-OCH₃ | 2-OH | COCH₃ |
| COCH₂CH₃ | 4-OH | 2-CH₃ | H |
| COCH₂CH₃ | 5-SH | 2-CH₃ | H |
| COCH₂CH₃ | 5-SH | 3-OCH₃ | H |
| COCH₂CH₃ | 3-SH | 4-OH | COCH₂CH₃ |
| COCH₂CH₃ | 3-CF₃ | 2-CH₃ | H |
| COCH₂CH₃ | 6-CF₃ | 2-OCH₃ | H |
| COCH₂CH₃ | 2-CF₃ | 5-OH | COCH₂CH₃ |
| COCH₂CH₃ | 3-CF₃ | 4-F | H |
| COCH₂CH₃ | 3-CF₃ | 4-Cl | H |
| COCH₂CH₃ | 2-CF₃ | 4-Br | H |
| COCH₂CH₃ | 2-CF₃ | 4-OH | H |
| H | 2-Cl | H | H |
| H | 2-F | H | H |
| H | 4-Br | H | COCH₃ |
| H | 3-Cl | H | H |
| H | 3-F | H | COCH₂CH₃ |

-continued

| R₁ | X | Y | R₂ |
|---|---|---|---|
| H | 2-CH₃ | H | H |
| H | 2-n-C₄H₉ | H | COCH₃ |
| H | 4-t-C₄H₉ | H | H |
| H | 3-C₂H₅ | H | H |
| H | 4-OCH₃ | H | H |
| H | 3-OC₂H₅ | H | H |
| H | 3-O-i-C₃H₇ | H | H |
| H | 4-O-n-C₄H₉ | H | COCH₂CH₃ |
| H | 2-OH | H | H |
| H | 4-OH | H | COCH₂CH₃ |
| H | 3-CN | H | H |
| H | 2-CF₃ | H | H |
| H | 3-CF₃ | H | COCH₃ |
| H | 4-CONH₂ | H | H |
| H | 2-SH | H | H |
| H | 3-SH | H | COCH₃ |
| H | 2-SCH₃ | H | H |
| H | 4-S-n-C₄H₉ | H | H |
| H | 2-SO₂CH₃ | H | COCH₃ |
| H | 4-SO₂-n-C₄H₉ | H | COCH₂CH₃ |
| H | 4-SO₂-i-C₃H₇ | H | H |
| H | 4-SO₂-t-C₄H₉ | H | COCH₂CH₃ |
| H | 3-SO₂NH₂ | H | H |
| H | 2-SO₃H | H | H |
| H | 3-SO₃H | H | COCH₃ |
| H | 4-CH₂OH | H | H |
| H | 3-COOC₂H₅ | H | H |
| H | 4-COO-n-C₄H₉ | H | H |
| H | 2,3-O—CH₂—O— | | H |
| H | 3,4-O—CH₂CH₂—O— | | COCH₃ |
| H | 2-Cl | 6-Cl | COCH₃ |
| H | 3-Cl | 4-Cl | COCH₂CH₃ |
| H | 2-F | 4-F | H |
| H | 3-Br | 5-Br | H |
| H | 2-Cl | 4-F | H |
| H | 4-Cl | 2-Br | COCH₃ |
| H | 3-Br | 4-F | H |
| H | 4-F | 3-CH₃ | COCH₂CH₃ |
| H | 2-CH₃ | 6-Cl | H |
| H | 2-CH₃ | 6-CH₃ | H |
| H | 2-CH₃ | 3-Br | H |
| H | 2-CH₃ | 3-OCH₃ | H |
| H | 3-CH₃ | 4-OH | COCH₃ |
| H | 2-OCH₃ | 4-OCH₃ | H |
| H | 5-OCH₃ | 2-OH | COCH₂CH₃ |
| H | 2-OH | 4-OH | H |
| H | 4-SH | 2-F | H |
| H | 2-SH | 3-Cl | COCH₃ |
| H | 2-SH | 5-Br | H |
| H | 2-CF₃ | 4-F | COCH₃ |
| H | 5-CF₃ | 2-Cl | H |
| H | 4-OH | 3-Br | H |
| H | 4-OH | 2-Cl | COCH₂CH₃ |
| H | 2-CF₃ | 4-Br | H |
| H | 2-SH | 4-OH | H |
| H | 5-SH | 2-CH₃ | H |
| H | 3-OCH₃ | 4-F | COCH₃ |
| H | 2-SH | 5-OCH₃ | H |

EXAMPLE 34

11,2′-Diacetyl-4″-deoxy-4″-anilino-oleandomycin

To a solution of aniline hydrochloride (4.1 g., 32 mmoles) in isopropanol (55 ml.) at 0° C. under a nitrogen atmosphere is added 11,2′-diacetyl-4″-deoxy-4″-oxo-oleandomycin (5.0 g., 6.5 mmoles). The reaction mixture is stirred for a half-hour at 0° C. and then sodium cyanoborohydride (296 mg., 4.7 mmoles) in isopropanol (15 ml.) is added over a period of 1.5 hours. The reaction mixture is stirred at 0° C. for two hours following completion of addition and is then poured into water (200 ml.) layered with ethyl acetate (200 ml.). The pH is adjusted to 9.5 with aqueous sodium hydroxide, and the aqueous phase discarded. The ethyl acetate solution which contains the desired product is then worked up according to the procedure of Example 1. The product is contained in fractions 130–180 and is isolated by concentration of the eluate under reduced pressure as a white foam (1.5 g.).

Its NMR spectrum showed only a single peak at $\delta_{CDCl_3}^{TMS}$ (ppm) of 3.18.

The 2′-acetyl group is solvolyzed as follows. A solution of 11,2′-diacetyl-4″-deoxy-4″-anilino-oleandomycin (400 mg.) in methanol (20 ml.) under a nitrogen atmosphere is stirred at room temperature for 18 hours. It is then evaporated to dryness under reduced pressure and the residue taken up in ether. Upon standing, the 11-monoacetyl derivative precipitates. It is filtered, washed with ether and dried in vacuo; m.p. 206°–208° C.

NMR $\delta_{CDCl_3}^{TMS}$ (ppm): 6.90 (m, 5H), 3.38 (s, 3H), 2.66 (m, 2H), 2.30 (s, 6H), 2.06 (s, 3H).

EXAMPLE 35

11,2′-Diacetyl-4″-deoxy-4″-anilino-oleandomycin (by acetylation of 11-monoacetyl derivative)

Acetic anhydride (0.071 ml., 7.6 mmoles) is added to a solution of 11-monoacetyl-4″-deoxy-4″-anilino-oleandomycin (615 mg., 0.76mmoles) in benzene (15 ml.) under a nitrogen atmosphere at room temperature. The mixture is stirred for three hours and is then poured into water (25 ml.) layered with benzene (25 ml.). The pH is adjusted to 9.5 with 6N NaOH and the benzene layer separated. It is washed successively with water and brine and then dried (Na₂SO₄) and concentrated under reduced pressure to a foam (600 mg.).

Its NMR spectrum showed peaks at $\delta_{CDCl_3}^{TMS}$ (ppm) of 3.22 and 3.18, indicative of a mixture of epimers.

EXAMPLE 36

General Procedure — Condensation of 11-Acetyl-4″-Deoxy-4″-Amino-oleandomycin with an Aromatic Aldehyde 11-Acetyl-4″-deoxy-4″-furfurylamino-oleandomycin To a solution of 11-acetyl-4″-deoxy-4″-amino-oleandomycin (5.0 g., 6.8 mmol.) in methanol (15 ml.) at −10° C. and under a nitrogen atmosphere is rapidly added with stirring a solution of furfural (1.65 g., 17.2 mmol), acetic acid (0.41 g., 6.8 mmol.) and methanol (20 ml.). Then, a solution of sodium cyanoborohydride (0.37 g. (85%), 5.0 mmol.) in methanol (20 ml.) is added over a 40 minute period while maintaining the temperature at about −10° to −5° C. Upon completion of addition, the reaction mixture is stirred at about −5° C. for 75 minutes and is then poured into water (150 ml.) layered with ether (150 ml.). The aqueous phase is adjusted to pH 3, separated, and is then extracted with 1N aqueous sodium hydroxide at pH 9–10. The ether extract is dried (Na₂SO₄) and evaporated to give 2.4 g. of the title product as a white foam. It is purified by chromatography on silica gel (200 g.) using chloroform-methanol (95:5) as eluant. The desired product is the first material to be eluted. The first 200 ml. of eluant were combined and evaporated to give the title product (470 mg., 8.5%) as an amorphous white foam. The product is a mixture of C.4″ epimers.

$^1$H NMR (60 MH$_z$) $\delta_{CDCl_3}^{TMS}$(ppm): 7.3 (m, 1H), 6.16 (m, 2H), 3.87 (s, 2H), 3.12 (s, 3H), 2.67 (bs, 2H), 2.28 (s, 6H), 2.03 (s, 3H).

EXAMPLE 37

General Procedure — Condensation of 11-Acetyl-4''-Deoxy-4''-Oxo-oleandomycin with an Aralkylamine 11-Acetyl-4''-deoxy-4''-(6-methyl-2-pyridylmethylamino)-oleandomycin A solution of 2-aminomethyl-6-methylpyridine (8.36 g., 68 mmol.) in acetic acid (4.1 g., 68 mmol.) and methanol (20 ml.) is rapidly added with stirring to a solution of 11-acetyl-4''-deoxy-4''-oxo-oleandomycin (5.0 g., 68 mmol.) in methanol (15 ml.) under a nitrogen atmosphere at room temperature. Then, a solution of sodium cyanoborohydride (0.37 g. [85%], 5.0 mmol.) in methanol (15 ml.) is added and the reaction mixture stirred for one-half hour. It is then poured into water (150 ml.) layered with ether (150 ml.). The aqueous phase is adjusted to pH 3, separated, adjusted to pH 10 with 1N sodium hydroxide solution and extracted with ether. The pH is then raised to 11.6 and the aqueous phase again extracted with ether. The combined extracts are dried (Na$_2$SO$_4$) and evaporated to give 11-acetyl-4''-deoxy-4''-(6-methyl-2-pyridylmethylamino)-oleandomycin (634 mg., 11%) as a light yellow foam. It is a mixture of the C.4'' epimers.

Its NMR spectra is:
$^1$H NMR (60 MHz) $\delta_{CDCl_3}^{TMS}$ (ppm): 6.80–7.60 (m, 3H), 4.00 (s, 2H), 3.35 (s, 3H), 2.63 (bs, H), 2.35 (s, 3H), 2.28 (s, 6H), 2.05 (s, 3H).

The following compounds are prepared by the procedures of Examples 36 or 37 from the appropriate reactants. A mixture of C.4'' epimers is produced in each instance by the process of Example 36. The process of Example 37 affords predominantly a single epimer, the stereochemistry of which is not yet established.

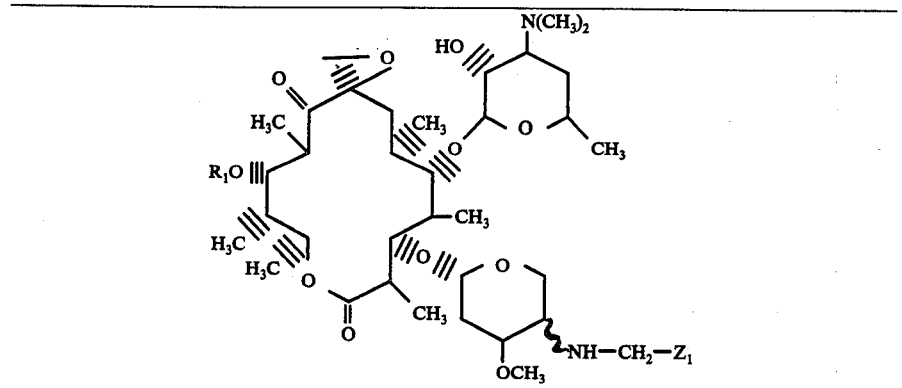

| Example | R$_1$ = acetyl Z$_1$ | Procedure | $^1$H NMR (60 MHz)$\delta_{CDCl_3}^{TMS}$ (ppm) |
|---|---|---|---|
| 38 | —C$_6$H$_5$. | 36 | 7.27–7.33(m,5H), 3.90(s,2H), 3,23(s,3H), 2.63(bs,2H), 2.28 (s,6H), 2.03 (s,3H). |
| 39 | 4-ClC$_6$H$_4$ | 37 | 7.3(s,4H), 3.88(s,2H), 3.26(s,3H), 2.63(d,2H), 2.3 (s,6H), 2.03(s,3H). |
| 40 | 3-ClC$_6$H$_4$ | 37 | 7.20–7.40(m,4H), 3.93(s,2H), 3.31(s,2H), 3.31(s,3H), 2.66(d,2H), 2.33 (s,6H), 2.10(s,3H). |
| 41 | 4-HOC$_6$H$_4$ | 36 | 6.6–7.6(m,4H), 3.33(s,3H), 2.66(d,2H), 2.33(s,6H), 2.06 (s,3H). |
| 42 | 4-CH$_3$OC$_6$H$_4$ | 37 | 6.7–7.3(m,4H), 3.80(s,5H), 3.35(s,3H), 2.65(bs,2H), 2.28 (s,6H), 2.05(s,3H). |
| 43 | 4-CH$_3$C$_6$H$_4$* | 37 | 7.0–7.3(m,4H), 3.85(s,2H), 3.35(s,3H), 2.65(bs,2H), 2.33 (s,3H), 2.38(s,6H), 2.06(s,3H). |
| 44 | 4-C$_6$H$_4$-C$_6$H$_5$ | 36 | 7.2–7.8(m,)H), 3.93(s,2H), 3.23(s,3H), 2.60(d,2H), 2.26 (s,6H), 2.00(s,3H). |
| 45 | 4-CH$_3$OC$_6$H$_4$* | 37 |  |
| 46 | 3-Cl-4-HOC$_6$H$_3$ | 36 | 6.78–7.33(m,3H), 3.78(s,2H), 3.25(s,3H), 2.63(bs,2H), 2.28 (s,6H), 2.03(s,3H). |
| 47 | 3,4-(Cl)$_2$C$_6$H$_3$ | 37 | 7.2–7.6(m,3H), 3.93(s,2H), 3.33(s,3H), 2.66(d,2H), 2.31 (s,6H), 2.08(s,3H). |
| 48 | 2-thienyl | 36 | 6.8–7.4(m,3H), 5.06(s,2H), 3.33(s,3H), 2.72(s,2H), 2.33 (s,6H), 2.10(s,3H). |
| 49 | 5-methyl-2-thienyl | 36 | 6.38–6.72(m,2H), 3.98(s,2H), 3.31 and 3.25 ( ,3H), 2.61 (d,2H), 2.43(s,3H), 2.28(s,6H), 2.03(s,3H). |
| 50 | 5-bromo-2-thienyl | 36 | 6.65–7.00(m,2H), 4.08(s,2H), 3.40 and 3.35 ( ,3H), 2.66 (bs,2H), 2.33(s,6H), 2.08(s,3H). |
| 51 | 2-furyl | 36 | 7.3(m,1H), 6.16(m,2H), 3.87(s,2H), 3.12(s,3H), 2.67(bs,2H), 2.28(s,6H), 2.03(s,3H). |
| 52 | 5-methyl-2-furyl | 36 | 5.93(d,2H), 3.83(s,2H), 3.23(s,3H), 2.66(bs,2H), 2.30(s,9H), 2.06(s,3H). |
| 53 | 5-hydroxymethyl-2-furyl | 36 | 6.15(b,2H), 4.55(s,2H), 3.86(s,2H), 3.23(s,3H), 2.66(bs,2H), 2.30(s,6H), 2.05(s,3H). |
| 54 | 2-tetrahydrofuryl | 37 | 3.35(s,3H), 2.63(bs,2H), 2.30(s,6H), 2.01(s,3H). |
| 55 | 2-tetrahydropyranyl | 37 | 3.43(s,3H), 2.68(bs,2H), 2.35(s,6H), 2.10(s,3H). |
| 56 | 2-Δ$^5$-dihydropyranyl | 37 | 6.33(bd,1H), 3.35(s,3H), 2.61(bs,2H), 2.28(s,6H), 2.05(s, 3H). |
| 57 | 2-pyridyl | 37 | 8.56(bd,1H), 7.1–7.8(m,3H), 4.13(s,2H), 3.35(s,3H), 2.70 (d,2H), 2.33(s,6H), 2.06(s,3H). |
| 58 | 2-pyridyl* | 37 |  |
| 59 | 3-pyridyl | 37 | 4.01(s,2H), 3.35(s,3H), 2.66(bs,2H), 2.31(s,6H), 2.08(s,3H). |
| 60 | 4-pyridyl | 37 | 8.60(d,2H), 7.36(bd,2H), 4.00(s,2H), 3.33(s,3H), 2.66(bs, 2H), 2.28(s,6H), 2.06(s,3H). |
| 61 | 6-methyl-2-pyridyl | 37 | 6.8–7.6(m,3H), 4.00(s,2H), 3.35(s,3H), 2.63(bs,2H), 2.35 (s,3H), 2.28(s,6H), 2.05(s,3H). |
| 62 | 5-methyl-2-pyridyl | 36 | 8.38(bs,1H), 7.0–7.6(m,2H), 4.03(s,2H), 3.30(s,2H), 2.67 |

-continued

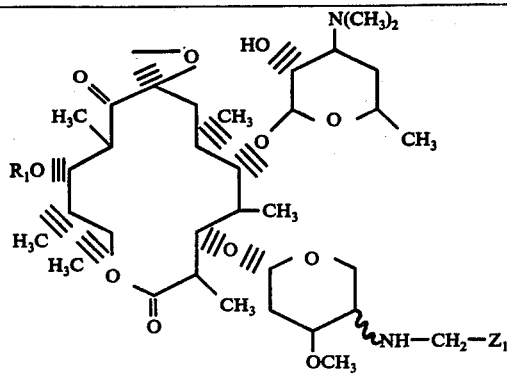

| Example | $R_1$ = acetyl $Z_1$ | Procedure | $^1$H NMR (60 MHz)$\delta^{TMS}_{CDCl_3}$ (ppm) |
|---|---|---|---|
| 63 | 3-methyl-2-pyridyl | 36 | (bs,2H), 2.33(s,9H), 2.06(s,3H). 8.33(bs,1H), 6.83–7.5(m,2H), 4.00(s,2H), 3.23(s,3H), 2.66 bs,2H), 2.33(s,3H), 2.30(s,6H), 2.03(s,3H). |
| 64 | 3-hydroxy-2-pyridyl | 36 | 7.0–8.0(m,3H), 3.40(s,3H), 2.68(d,2H), 2.31(s,6H), 2.08 (s,3H). |
| 65 | 2-pyrrolyl | 36 | 6.78(m,1H), 5.92–6.25(m,2H), 4.01(s,2H), 3.35(s,3H), 2.70 (bs,2H), 2.33(s,6H), 2.08(s,3H). |
| 66 | 1-methyl-2-pyrrolyl | 36 | 6.62(m,1H), 6.05(m,2H), 3.92(s,2H), 3.75(s,3H), 3.26(s,3H), 2.68(bs,2H), 2.31(s,6H), 2.06(s,3H). |
| 67 | 5-chloro-2-pyridyl | | 8.46(m,1H), 7.50–7.66(m,2H), 4.08(s,2H), 3.33(s,3H), 2.66 (d,2H), 2.30(s,6H), 2.06(s,3H). |
| 68 | 2-pyridyl | 37 | 8.4–8.6(m,1H), 6.9–7.8(m,3H), 3.30(s,3H), 2.66(d,2H), 2.30 (s,6H), 2.06(s,3H). |
| 69 | 1-morpholino | 37 | 3.36(s,3H), 2.30(s,6H), 2.06(s,3H). |
| 70+ | —C$_6$H$_5$ | 37 | 7.0(s,5H), 3.39(s,2H), 3.30(s,3H), 2.83(d,2H), 2.33(s,6H). |
| 71+ | 4-ClC$_6$H$_4$ | 37 | 7.33(s,4H), 3.90(s,2H), 3.33(s,3H), 2.83(d,2H), 2.33(s,6H). |
| 72+ | -3-ClC$_6$H$_4$ | 37 | 7.2–7.6(m,4H), 3.93(s,2H), 3.30(s,3H), 2.83(d,2H), 2.33 (s,6H). |

\*=single epimer (separated chromatographically on silica gel according to Example 36)
+-$R_1$ = H

EXAMPLE 73

Utilizing the procedures of Examples 36 and 37, the compounds listed below are prepared from appropriate reactants. When using an 11,2'-dialkanoyl-4"-deoxy-4"-oxo(or 4"-amino)-oleandomycin as reactant, isopropanol is used as solvent to avoid hydrolysis of the 2'-alkanoyl group.

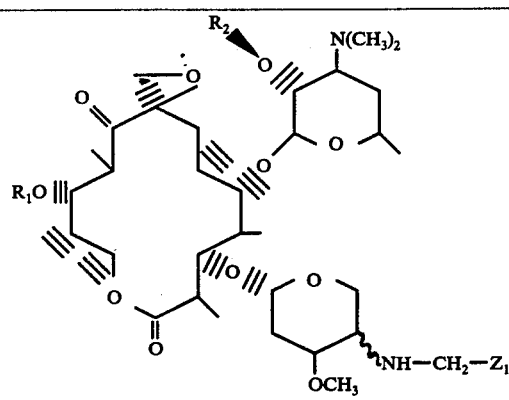

| $R_1$ | $R_2$ | $Z_1$ | Method |
|---|---|---|---|
| Pr | H | —C$_6$H$_5$ | 36 |
| Pr | H | 4-ClC$_6$H$_4$ | 36 |
| Pr | H | 4-HOC$_6$H$_4$ | 37 |
| Pr | H | -3-CH$_3$OC$_6$H$_4$ | 37 |
| Pr | H | -2-CH$_3$C$_6$H$_4$ | 37 |
| Pr | H | 4-C$_2$H$_5$C$_6$H$_4$ | 36 |
| Pr | H | 4-CH$_3$OC$_6$H$_4$ | 37 |
| Pr | H | -2-HOCH$_2$C$_6$H$_4$ | 37 |
| Pr | H | -3-HOCH$_2$C$_6$H$_4$ | 37 |
| Pr | H | -3-BrC$_6$H$_4$ | 37 |
| Pr | H | 4-FC$_6$H$_4$ | 37 |
| Pr | H | 4-HSC$_6$H$_4$ | 37 |

-continued

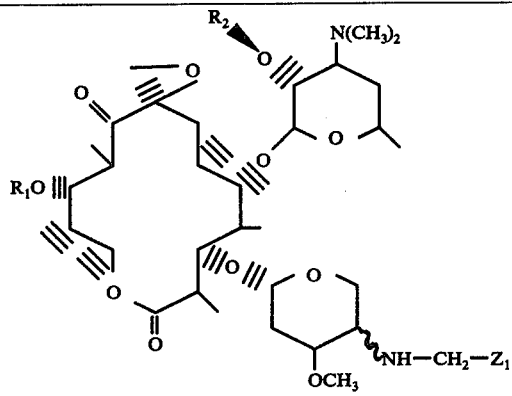

| $R_1$ | $R_2$ | $Z_1$ | Method |
|---|---|---|---|
| Pr | H | -3-CF$_3$C$_6$H$_4$ | 37 |
| Pr | H | 4-(CH$_3$)$_2$NC$_6$H$_4$ | 37 |
| Pr | H | -3-CNC$_6$H$_4$ | 37 |
| Pr | H | 4-n-C$_3$H$_7$C$_6$H$_4$ | 36 |
| Pr | H | 4-n-C$_4$H$_9$OC$_6$H$_4$ | 36 |
| Pr | H | -3-C$_2$H$_5$C$_6$H$_4$ | 36 |
| Pr | H | 4-CH$_3$SC$_6$H$_4$ | 36 |
| Pr | H | 4-C$_2$H$_5$SO$_2$C$_6$H$_4$ | 36 |
| Ac | H | 4-HOCH$_2$C$_6$H$_4$ | 37 |
| Ac | H | 4-CF$_3$C$_6$H$_4$ | 37 |
| Ac | H | -2-FC$_6$H$_4$ | 36 |
| Ac | H | 4-BrC$_6$H$_4$ | 36 |
| Ac | H | -3-(CH$_3$)$_2$NC$_6$H$_4$ | 37 |
| Ac | H | 4-CNC$_6$H$_4$ | 37 |
| Ac | H | 4-t-C$_4$H$_9$C$_6$H$_4$ | 37 |
| Ac | H | 4-n-C$_3$H$_7$OC$_6$H$_4$ | 36 |
| Ac | H | 4-n-C$_4$H$_9$C$_6$H$_4$ | 37 |
| Ac | H | -3-i-C$_3$H$_7$SC$_6$H$_4$ | 36 |
| Ac | H | 4-HO$_3$SC$_6$H$_4$ | 36 |
| Ac | H | -3-HO$_3$SC$_6$H$_4$ | 36 |
| Ac | H | -3-H$_2$NCOC$_6$H$_4$ | 36 |
| Ac | H | 4-H$_2$NSO$_2$C$_6$H$_4$ | 36 |
| Ac | H | -2-H$_3$COCOC$_6$H$_4$ | 36 |

-continued

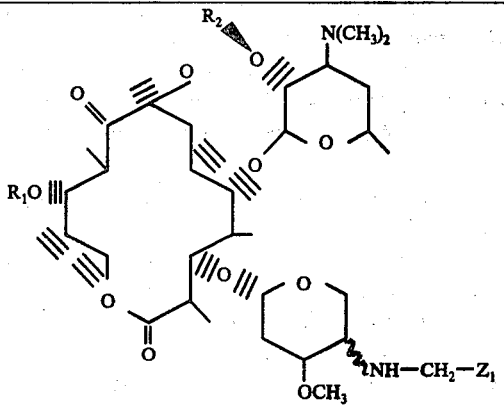

| R₁ | R₂ | Z₁ | Method |
|---|---|---|---|
| Ac | H | -4-H₄C₉OCOC₆H₄ | 36 |
| Pr | H | -4-H₄C₂OCOC₆H₄ | 36 |
| Pr | H | -2-HO₃SC₆H₄ | 36 |
| Pr | H | -3-H₂NCOC₆H₄ | 36 |
| Ac | Ac | —C₆H₅ | 37 |
| Ac | Ac | 4-ClC₆H₄ | 37 |
| Ac | Ac | 4-CH₃OC₆H₄ | 37 |
| Ac | Ac | 4-HOCH₂C₆H₄ | 36 |
| Ac | Ac | -2-HO₃SC₆H₄ | 36 |
| Ac | Ac | -2-CH₃SO₂C₆H₄ | 36 |
| Pr | Pr | —C₆H₅ | 36 |
| Pr | Pr | -3-C₆H₄C₆H₅ | 36 |
| Pr | Pr | -4-H₂NSO₂C₆H₄ | 36 |
| Pr | Pr | -2-CF₃C₆H₄ | 36 |
| Ac | H | -3,5-(CH₃)₂C₆H₃ | 37 |
| Ac | H | -2,6-(CH₃O)₂C₆H₃ | 37 |
| Ac | H | -3,5-(F)₂C₆H₃ | 36 |
| Ac | H | -2,4-(Br)₂C₆H₃ | 36 |
| Ac | H | -3,4-(HO)₂C₆H₃ | 36 |
| Pr | H | -2,4-(HO)₂C₆H₃ | 36 |
| Pr | H | -2-Br-5-HOC₆H₃ | 36 |
| Pr | H | -4-Cl-3-FC₆H₃ | 36 |
| Pr | H | -2,3-(OCH₂O)C₆H₃ | 36* |
| Ac | H | -3,4-(OCH₂CH₂O)C₆H₃ | 36* |
| Ac | H | -3-CH₃-6-ClC₆H₃ | 36* |
| H | H | —C₆H₅ | 37 |
| H | H | -2-ClC₆H₄ | 37 |
| H | H | -2,6-(Cl)₂C₆H₃ | 36 |
| H | H | -2,4-(HO)₂C₆H₃ | 36 |
| H | H | -3-Cl-4-HOC₆H₃ | 36 |
| H | H | -2-HO₃SC₆H₄ | 36 |
| H | H | -4-C₂H₅C₆H₄ | 36 |
| H | H | -3-CH₃OC₆H₄ | 37 |
| H | H | -2,5-(CH₃O)₂C₆H₃ | 37 |
| H | H | -2-HOCH₂C₆H₄ | 36 |
| H | H | -3-(CH₃)₂NC₆H₄ | 36 |
| H | H | -4-H₂NSO₂C₆H₄ | 36 |
| H | H | -2-Cl-6-FC₆H₃ | 36 |
| H | H | -4-HO-3-CH₃OC₆H₃ | 36 |
| H | H | -2,3-(OCH₂O)C₆H₃ | 36* |
| H | H | -3-Br—C₆H₄ | 36 |
| H | H | -2-C₂H₅C₆H₄ | 37 |
| Ac | H | -4-i-C₄H₉OC₆H₄ | 37 |
| Ac | H | -2-CH₃SO₂C₆H₄ | 36 |
| H | H | -4-C₄H₉C₆H₄ | 37 |
| H | H | -4-CF₃C₆H₄ | 36 |
| H | H | -2-C₂H₅OCOC₆H₄ | 36 |
| H | H | -3-H₂NCOC₆H₄ | 36 |
| H | H | -3-CNC₆H₄ | 36 |
| H | H | -2-HSC₆H₄ | 36 |
| Ac | H | -3-CH₃-6-SHC₆H₃ | 36 |
| H | H | -2-CH₃-5-FC₆H₃ | 36 |
| H | H | -3-CH₃-6-CH₃SC₆H₃ | 36 |
| H | H | -2-Br-4-CH₃C₆H₃ | 36 |
| Pr | H | -2-C₄H₉O-5-ClC₆H₃ | 36 |
| Ac | Ac | -2-CH₃-4-HOC₆H₃ | 36 |
| Ac | Ac | -3-C₂H₅O-4-HOC₆H₃ | 36 |
| Ac | Ac | -4-n-C₃H₇SO₂C₆H₄ | 36 |
| Pr | Pr | -2,5-(CH₃O)₂C₆H₃ | 37 |
| Pr | H | -4-HSC₆H₄ | 36 |
| Ac | Ac | -2-Cl-3-HOC₆H₃ | 37 |
| Ac | H | -3-thienyl | 36 |
| Ac | H | -5-Cl-2-thienyl | 36 |
| Ac | H | -3-Br-2-thienyl | 36 |
| Ac | H | -3-HO-2-thienyl | 36 |
| Ac | H | -5-Br-3-thienyl | 36 |
| Ac | H | -5-Cl-2-furyl | 36 |
| Ac | H | -2-Cl-3-furyl | 36 |
| Ac | H | 4-HOCH₂-3-furyl | 36 |
| Ac | H | -6-Br-2-pyridyl | 36 |
| Ac | H | -3-HO-4-pyridyl | 36 |

-continued

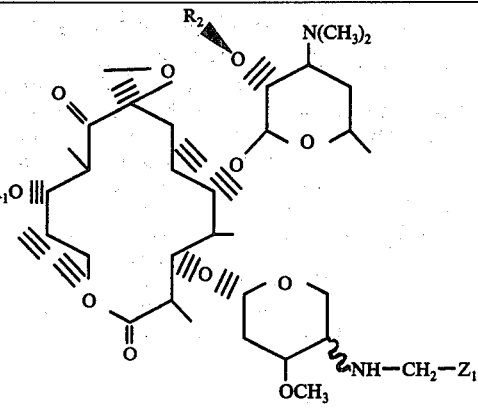

| R₁ | R₂ | Z₁ | Method |
|---|---|---|---|
| Ac | Ac | -3-thienyl | 36 |
| Ac | Ac | -2-CH₃-4-pyridyl | 36 |
| Ac | Ac | -4-Br-2-pyrrolyl | 36 |
| Pr | H | -3-pyrrolyl | 36 |
| Pr | H | -1-CH₃-2-pyrrolyl | 36 |
| Pr | H | -6-HOCH₂-2-pyridyl | 36 |
| Pr | Pr | -2-pyridyl | 36 |
| Pr | Pr | -3-HO-2-pyridyl | 36 |
| Pr | Pr | -2-dihydropyranyl | 36 |
| H | H | -2-pyridyl | 36 |
| H | H | -2-thienyl | 36 |
| H | H | -4-Br-2-pyrrolyl | 36 |

EXAMPLE 74

Acid Addition Salts

To a solution of 11-acetyl-4''-deoxy-4'''-(2-fluoroanilino)-oleandomycin (1.0 mmole) in methanol (50 ml.) is added an equimolar proportion of hydrogen chloride and the reaction mixture stirred at room temperature for one hour. Removal of the solvent by evaporation affords the hydrochloride salt.

In like manner, the above-named compound and the compounds of Examples 1–73 are converted to their hydrochloride, hydrobromide, sulfate, acetate, butyrate, citrate, glycolate, tartrate, stearate, pamoate, fumarate, benzoate and aspartate salts.

When the reactant is an 11,2'-dialkanoyl-4''-deoxy-4'''-anilino-oleandomycin, isopropanol is used as solvent.

PREPARATION A

11,2'-Diacetyl-4''-deoxy-4''-oxo-oleandomycin

To 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 minutes, the contents are cooled to −25° C. and treated with 5.0 g. of 11,2'-diacetyl-oleandomycin in 100 ml. of toluene. Cooling and stirring are continued for 2 hours followed by the addition of 4.73 ml. of triethylamine. The reaction mixture is allowed to stir at 0° C. for 15 minutes, and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR (60 MHz) $\delta_{CDCl_3}^{TMS}$ (ppm): 3.48 (s, 3H), 2.61 (m, 2H), 2.23 (s, 2H), and 2.03 (s, 6H).

In like manner, the following 11,2'-dialkanoyl-4''-deoxy-4''-oxooleandomycins are prepared from the corresponding 11,2'-dialkanoyl-oleandomycins:

11,2'-dipropionyl-
11-acetyl-2'-propionyl
11-propionyl-2'-propionyl-

PREPARATION B

11-Acetyl-4"-deoxy-4"-oxo-oleandomycin

A solution of 4.0 g. of 11,2'-diacetyl-4"-deoxy-4"-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°-117° C.

NMR (60 MHz) $\delta_{CDCl_3}^{TMS}$ (ppm): 3.43 (s, 3H), 2.60 (m, 2H), 2.23 (s, 6H), and 2.01 (s, 3H).

Following the above procedures, 11-propionyl-4"-deoxy-4"-oxooleandomycin is prepared from 11,2'-dipropionyl-4"-deoxy-4"-oxo-oleandomycin.

PREPARATION C

2'-Acetyl-4"-deoxy-4"-oxo-oleandomycin

Dimethylsulfide (0.337 ml.) is added to a turbid solution of 467 mg. of N-chlorosuccinimide in 20 ml. of toluene and 6 ml. of benzene cooled to −5° C. and maintained under a nitrogen atmosphere. After stirring at 0° C. for 20 minutes the mixture is cooled to −25° C. and 1.46 g. of 2'-acetyloleandomycin and 15 ml. of toluene are added. Stirring is continued for 2 hours at −20° C. followed by the addition of 0.46 ml. of triethyl amine. The reaction mixture is maintained at −20° C. for an additional 5 minutes and then allowed to warm to 0° C. The mixture is poured, with stirring, into 50 ml. of water and 50 ml. of ethyl acetate. The pH of the aqueous mixture is adjusted to 9.5 by addition of aqueous sodium hydroxide solution. The organic layer is subsequently separated, dried over sodium sulfate and concentrated in vacuo to a white foam (1.5 g.). Trituration with diethyl ether gives 864 mg. of crude product, which on recrystallization twice from methylene chloride-diethyl ether gives 212 mg. of the pure product, m.p. 183°-185.5° C.

Anal. Calc'd for $C_{37}H_{61}O_{13}N$: C, 61.1; H, 8.5; N, 1.9. Found: C, 60.9; H, 8.4; N, 1.9.

NMR (60 MHz) $\delta_{CDCl_3}^{TMS}$ (ppm): 5.60 (m, 1H), 3.50 (s, 3H), 2.73 (m, 2H), 2.23 (s, 6H) and 2.03 (s, 3H).

In like manner, 2'-propionyl-4"-deoxy-4"-oxo-oleandomycin is prepared from 2'-propionyloleandomycin.

PREPARATION D

4"-Deoxy-4"-oxo-oleandomycin

A solution of 1.0 g. of 2'-acetyl-4"-deoxy-4"-oxo-oleandomycin in 20 ml. of methanol is allowed to stir at room temperature overnight. The solution is concentrated in vacuo to give the desired product as a white foam, 937 mg.

NMR (60 MHz) $\delta_{CDCl_3}^{TMS}$ (ppm): 5.60 (m, 1H), 3.50 (s, 3H), 2.85 (m, 2H), and 2.26 (s, 6H).

Similarly, 2'-propionyl-4"-deoxy-4"-oxo-oleandomycin is hydrolyzed to 4"-deoxy-4"-oxo-oleandomycin.

PREPARATION E

11-Acetyl-4"-deoxy-4"-amino-oleandomycin

To a suspension of 10% palladium-on-charcoal (10 g.) in methanol (100 ml.) is added ammonium acetate (21.2 g.) and the resulting slurry is treated with a solution of 11-acetyl-4"-deoxy-4"-oxo-oleandomycin (20 g.) in 100 ml. of the same solvent. The suspension is shaken at room temperature in a hydrogen atmosphere at an initial pressure of 50 p.s.i. After 1.5 hours, the catalyst is filtered and the filtrate is added with stirring to a mixture of water (1200 ml.) and chloroform (500 ml.). The pH is adjusted from 6.4 to 4.5 and the organic layer is separated. The aqueous layer, after a further extraction with chloroform (500 ml.), is treated with ethyl acetate (500 ml.) and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°-160° C.

NMR (δ, CDCl$_3$): 3.41 (3H)s, 2.70 (2H)m, 2.36 (6H)s and 2.10 (3H)s.

The other epimer, which exists in the crude foam to the extent of 20-25%, is obtained by gradual concentration and filtration of the mother liquors.

In like manner, the following mono-alkanoyl and dialkanoyl esters of 4"-deoxy-4"-amino-oleandomycin are prepared from the appropriate mono-alkanoyl and dialkanoyl 4"-deoxy-4"-oxo-oleandomycins. When a 2'-ester is prepared, isopropanol is used as solvent.

11,2'-diacetyl-
2'-acetyl-
2'-propionyl-
4 11,2'-dipropionyl -dipropronyl-
11-propionyl-
11-acetyl-2'-propionyl-
11-propionyl-2'-acetyl-

PREPARATION F

4"-Deoxy-4"-amino-oleandomycin

A solution of 2'-acetyl- 4"-deoxy-4"-oxo-oleandomycin (20 g.) in methanol (125 ml.), after stirring at room temperature overnight, is treated with ammonium acetate (21.2 g.). The resulting solution is cooled in an ice bath and treated with sodium cyanoborohydride (1.26 g.). The cooling bath is then removed and the reaction mixture allowed to stir at room temperature for 2 hours. The reaction is poured into water (600 ml.) and diethyl ether (600 ml.) and the pH adjusted from 8.3 to 7.5. The ether layer is separated and the aqueous phase extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1x) and a saturated brine solution and dried over sodium sulfate. The latter extracts, taken at pH 9.9, are concentrated to a foam and chromatographed on silica gel (160 g.), using chloroform as the loading solvent and initial eluate. After eleven fractions, 12 ml. per fraction are taken, the eluate is changed to 5% methanol-95% chloroform. At fraction 370 the eluate is changed to 10% methanol-90% chloroform and at fraction 440, 15% methaol-85% chloroform is used. Fractions 85-260 are combined and concentrated in vacuo to dryness to provide 2.44 g. of the desired product.

NMR (δ, CDCl$_3$): 5.56 (1H)m, 3.36 (3H)s, 2.9 (2H)m and 2.26 (6H)s.

What is claimed is:

1. An epimeric compound having the formula

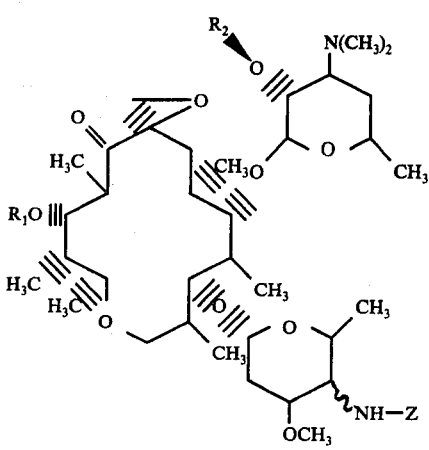

and the pharmaceutically acceptable salts thereof wherein
  each of $R_1$ and $R_2$ is selected from the group consisting of hydrogen, alkanoyl having from two to three carbon atoms and is selected from the group consisting of acetyl and propionyl;
  Z is selected from the group consisting of a first subgroup consisting of

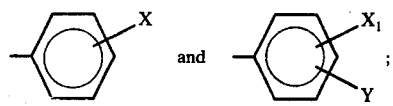

a second subgroup consisting of

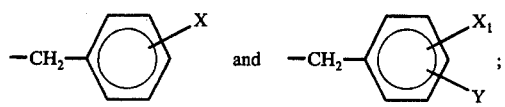

and a third subgroup consisting of

—CH$_2$-heterocyclyl;

wherein
  X is selected from the group consisting of hydrogen, chloro, bromo, fluoro, alkyl having from one to four carbon atoms, alkoxy having from one to four carbon atoms, hydroxy, mercapto, trifluoromethyl, N(CH$_3$)$_2$, cyano, thioalkyl having from one to four carbon atoms, sulfonylalkyl having from one to four carbon atoms, sulfamyl, sulfo, carbamyl, hydroxymethyl and carbalkoxy having from one to four carbon atoms in the alkoxy group;
  $X_1$ is selected from the group consisting of chloro, bromo, fluoro, methyl, methoxy, hydroxy, mercapto and trifluoromethyl;
  Y is selected from the group consisting of choro, bromo, fluoro, methyl, methoxy and hydroxy;
  and $X_1$ and Y when taken together are located on adjacent carbon atoms and are alkylenedioxy and are selected from the group consisting of methylenedioxy and ethylenedioxy;
  and heterocyclyl is selected from the group consisting of (a) thienyl, furyl, pyridyl and pyrrolyl and substituted derivatives thereof wherein the substituent is selected from the group consisting of methyl, chloro, bromo, hydroxy and hydroxymethyl; and (b) 2-tetrahydrofuryl, 2-dihydropyranyl, 2-tetrahydropyranyl and morpholino.

2. A compound according to claim 1 wherein Z is

$R_2$ is hydrogen and $R_1$ is alkanoyl.

3. A compound according to claim 2 wherein X is fluoro.

4. A compound according to claim 2 wherein X is alkoxy.

5. A compound according to claim 2 wherein X is alkyl.

6. A compound according to claim 2 wherein X is carbalkoxy.

7. A compound according to claim 3 wherein X is 2-fluoro and $R_1$ is acetyl.

8. A compound according to claim 4 wherein X is 4-methoxy and $R_1$ is acetyl.

9. A compound according to claim 6 wherein X is 2-carbomethoxy and $R_1$ is acetyl.

10. A compound according to claim 1 wherein Z is

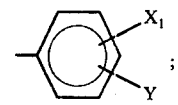

$R_2$ is hydrogen and $R_1$ is alkanoyl.

11. A compound according to claim 10 wherein $X_1$ is 3-chloro and Y is 4-chloro.

12. A compound according to claim 10 wherein $X_1$ is 2-methoxy and Y is 4-methoxy.

13. A compound according to claim 1 wherein Z is

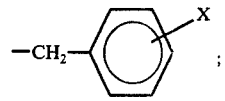

$R_2$ is hydrogen and $R_1$ is alkanoyl.

14. A compound according to claim 13 wherein x is chloro.

15. A compound according to claim 1 wherein Z is

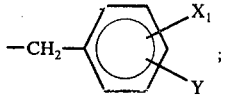

$R_2$ is hydrogen and $R_1$ is alkanoyl.

16. A compound according to claim 15 wherein $X_1$ is 3-chloro, Y is 4-chloro and $R_1$ is acetyl.

17. A compound according to claim 13 wherein $X_1$ is 4-hydroxy; Y is 3-chloro and $R_1$ is acetyl.

18. A compound according to claim 1 wherein Z is —CH$_2$-heterocyclyl wherein heterocyclyl is pyridyl; $R_2$ is hydrogen and $R_1$ is alkanoyl.

19. A compound according to claim 1 wherein Z is —CH$_2$-heterocyclyl wherein heterocyclyl is 2-dihydropyranyl; $R_1$ is acetyl and $R_2$ is hydrogen.

20. A compound according to claim 1 wherein Z is —CH$_2$-heterocyclyl wherein heterocyclyl is pyrrolyl; $R_1$ is alkanoyl and $R_2$ is hydrogen.

* * * * *

UNITED STATES PATENT OFFICE
CERTIFICATE OF CORRECTION

PATENT NO. : 4,090,017
DATED : May 16, 1978
INVENTOR(S) : Frank C. Sciavolino, East Lyme, Connecticut It is certified that error appears in the above-identified patent and that said Letters Patent are hereby corrected as shown below:

Title page, in the Title, "4-Deoxy-4" should read
-- 4"-Deoxy-4" --.

Signed and Sealed this

Sixth Day of March 1979

[SEAL]

Attest:

RUTH C. MASON
Attesting Officer

DONALD W. BANNER
Commissioner of Patents and Trademarks